Figure 1:
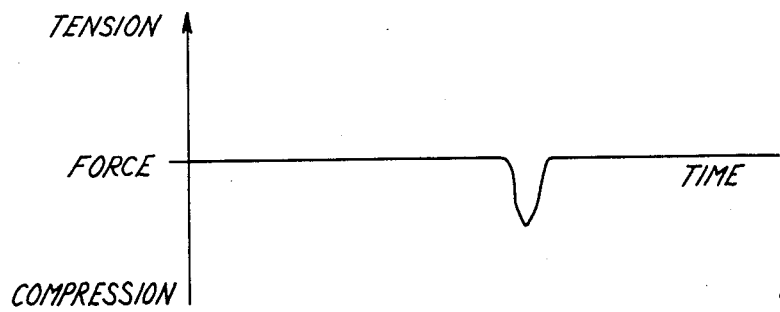

United States Patent [19]

Cawley et al.

[11] Patent Number: 4,542,639
[45] Date of Patent: Sep. 24, 1985

[54] TESTING OF STRUCTURES BY IMPACT

[75] Inventors: Peter Cawley, London; Robert D. Adams, Bristol, both of England

[73] Assignee: National Research Development Corporation, London, England

[21] Appl. No.: 596,154

[22] Filed: Apr. 2, 1984

[30] Foreign Application Priority Data

Mar. 31, 1983 [GB] United Kingdom ............... 83 09030

[51] Int. Cl.⁴ ...................... G01M 7/00; G01N 29/04
[52] U.S. Cl. .......................................... 73/12; 73/82; 73/582; 73/588
[58] Field of Search ...................... 73/12, 82, 818, 582, 73/588, 579, 584, 586

[56] References Cited

U.S. PATENT DOCUMENTS 4,470,293  9/1984  Redman .................................. 73/12
4,479,386  10/1984  Beggs et al. .......................... 73/582

FOREIGN PATENT DOCUMENTS 1175719  12/1969  United Kingdom .
1446661  8/1976  United Kingdom .
1482662  8/1977  United Kingdom .
1523295  8/1978  United Kingdom .

Primary Examiner—Donald O. Woodiel
Attorney, Agent, or Firm—Cushman, Darby & Cushman

[57] ABSTRACT

Apparatus and method for testing structures by impact. The structure is struck by an impactor associated with a force transducer the output of which is related to the force which the transducer experiences on impact and encompasses a frequency range including the lowest frequencies (typically approaching zero frequency, see FIG. 3) which that force contains to any substantial degree. A test spectrum of the force including that full range of frequencies is produced by a Fourier transformer in a form suitable for automatic comparison, and is then so compared with a reference spectrum typical of impact with a reference structure, and a signal is produced indicating fit or lack of fit between the test and reference spectra.

9 Claims, 5 Drawing Figures

TESTING OF STRUCTURES BY IMPACT

This invention relates to the testing of structures by impact. When a structure is tapped, the characteristics of the impact are dependent on the local impedance of the structure and on the impactor used. For many years it has been customary to test laminates by tapping them with a coin, and then judging their soundness by ear by listening to the resulting sound emitted by them.

In the relatively recent past, apparatus has become available that is capable of testing in a manner that is in some ways comparable but does not rely upon the senses of the operator. One such apparatus has comprised an electrically-actuated hammer, capable of striking a structure with a single impact of predetermined energy. A force transducer is attached to the hammer and the electrical output of the transducer is fed to an oscilloscope giving a display of the time history of the force input to the structure from the hammer. The display may then be compared by eye rather than by ear as traditionally, with reference displays on the oscilloscope resulting from impact of the same hammer with structures that are known to be either sound or unsound.

Although methods of testing using such apparatus clearly have many advantages over the traditional methods of testing involving the human ear, some disadvantages have also become apparent. One such disadvantage is that the characteristics of the force input vary directly with the energy with which the hammer strikes the specimen. The hammer must therefore be precision-made so that it always makes impact with substantially the same energy, and this is particularly hard to achieve if the hammer is to be capable of making impact with structures of different shape and size rather than with just a single type of structure. Another disadvantage is that the diferences between impacts on sound and damaged structures are often difficult to see from displays of the force-time histories.

Another such apparatus, described in UK Patent Specification No. 1482662, includes a stationary pressure transducer onto which a particle to be tested is allowed to drop, generating an electrical signal. The signal is fed to a high pass frequency filter, and any particle giving rise to a substantial output from that filter is deemed likely to be satisfactory whereas particles that generate only low frequencies that are taken out by the filter are deemed likely to be defective. The satisfactory character of those particles that generate an output from the filter may be confirmed by studying by eye either the time history or the frequency spectrum of that output.

Our invention results from appreciating the potential advantages of basing at test not upon the force-time history of the impact, or upon whether or not an impact generates signals containing frequencies above a certain threshold, but upon the automatic comparison of a frequency spectrum of the force input, taken over an appropriate range and appropriately presented, with a similar spectrum representing impact with a reference structure. In particular our invention arises from appreciating the usefulness, in connection with such automatic comparison, of including within the frequency range the lowest frequencies that occur to any substantial degree within the force input. According to the invention a method of testing a structure by the use of an impactor attached to a force transducer comprises causing the impactor to make impact with the structure, obtaining from the force transducer an output the magnitude of which is linearly related to the force to which the transducer is subjected by reason of the impact and so that the output encompasses a frequency range including the lowest frequencies which the force includes to any substantial degree, passing the output of the force transducer to a spectrum analyser to yield a test frequency spectrum of the output over the said frequency range in a form suitable for automatic comparison with a reference spectrum of similar form indicative of the same impactor striking a reference structure, so comparing the test and reference spectra automatically, and producing a signal indicative of a fit or lack of fit between the test and reference spectra.

The lower end of the frequency range may be substantially zero frequency and the upper end may be as high as about 30 kHz.

The output of the force transducer may be passed to the spectrum analyser not only during the duration of the impact but also for a short period afterwards, the generation of the test spectrum may be triggered by the magnitude of the output from the force transducer exceeding a preset value, and the method may include a "pre-trigger facility" whereby the test spectrum when generated includes information relating to a predetermined period occurring before the moment of triggering.

The spectra may be presented in a form in which force indicated on a logarithmic scale is plotted against frequency.

The signal indicative of a fit or lack of fit may be in various electrical forms, used for instance to generate a number or set up a VDU display, or to illuminate a red/green light or sound an alarm bell.

The invention also includes apparatus to carry out such methods, and the spectrum analyser may be in the form of a combination of an analogue-to-digital converter and a digital Fourier transformer adapted to receive the output of that converter.

Figure 2:
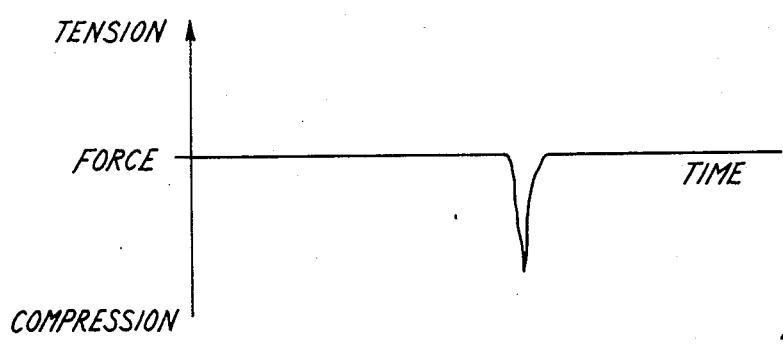
Figure 3:
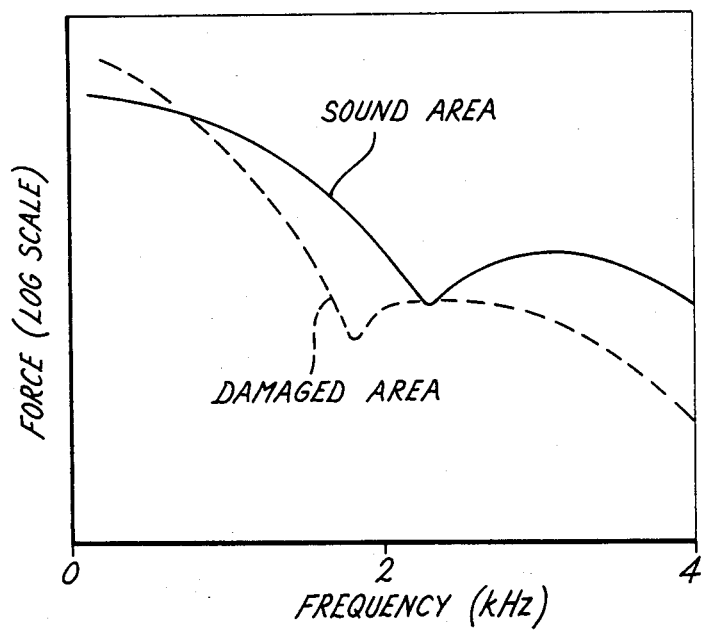
Figure 4:
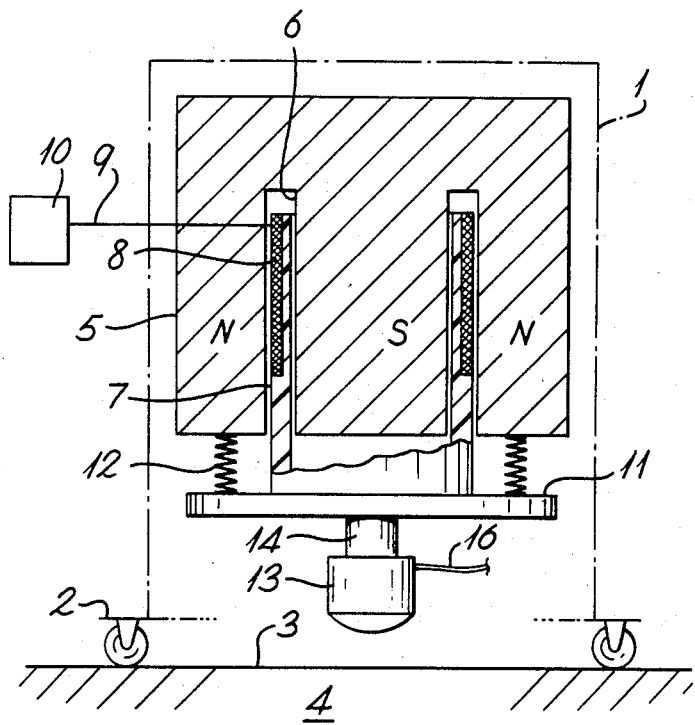

The invention is also defined by the claims at the end of this specification and will now be described, by way of example, with reference to the accompanying drawings in which:

FIGS. 1 to 3 are graphs;
FIG. 4 is a diagrammatic section through an impactor associated with a force transducer, and
FIG. 5 is a circuit diagram.

FIGS. 1 and 2 show typical force-time histories resulting from impactor taps on de-bonded (FIG. 1) and sound (FIG. 2) areas of an adhesively-bonded structure. In each of these figures the x-axis represents time and the y-axis represents the force to which the hammer is subjected, compression being indicated as negative and tension as positive. It is assumed that the impactor has made impact with each structure with equal energy. As comparison between the two figures clearly shows, when making impact with the sound structure the impactor undergoes an impact of greater maximum amplitude but shorter duration than when striking the damaged, de-bonded area. It may also be noted that although those two comparisons between the graphical functions of FIGS. 1 and 2 may easily be made, the functions themselves are not clearly of similar shape and neither of them has the form of a smooth curve. Electronic analysis of the curves is therefore difficult. In contrast FIG. 3 shows that if the frequency content of the force pulses is displayed, the difference between the impacts appears in a form more suitable for automatic comparison. In FIG. 3 the y-axis represents compressive force on a logarithmic scale, and the x-axis represents frequency in kHz, and the solid line corresponds to the same impact as that of FIG. 2 while the broken line corresponds to the same impact as that of FIG. 1. The two frequency functions of FIG. 3 may be derived from the force-time functions of the FIGS. 2 and 1 in a manner that will be described with reference to FIG. 5, but it may readily be seen from the broken-line function that when the impactor makes its impact with a damaged area it acquires a high porportion of energy at low frequencies but the energy content falls off rapidly with increasing frequency. As the solid line shows, however, when the impactor makes impact with a sound area it may acquire a relatively smaller proportion of its total energy at the lowest frequencies but the proportion decreases less rapidly as frequency rises. Three things particularly material to the invention are demonstrated by FIG. 3. Firstly the pronounced difference in magnitude between the two functions as they approach the lowest illustrated frequency—that is to say, zero frequency—and the fact that they are both of substantial magnitude at that frequency value. These low-frequency differences between the impacts on sound and damaged areas help greatly towards achieving a clear indication of fit or lack of fit when test and reference spectra are compared automatically according to the present invention. Secondly the lower upper frequency limit shown: while an upper limit as low as 4 kHz might actually be chosen for many applications, in practice some applications of the invention might benefit from a higher value, say up to 30 kHz. Thirdly it will be noted that the two functions shown in the solid and broken lines are both relatively smoothly curved and generally similar in shape, so that automatic comparison is relatively simple.

FIG. 4 shows a suitable impactor including a casing 1 attached to a trolley 2 which rests upon the surface 3 of the structure 4 that is to be tested. The casing houses a permanent magnet 5 formed with a ring-sectioned recess 6 inside which a hollow cylindrical former 7 fits with clearance and can move axially. Former 7 is wound with a coil 8, connected by leads 9 to a voltage source 10. Former 7 is fixed to a circular plate 11, which is in turn connected to magnets by a spring 12 so that the spring suspends the coil 7 in the field of the magnet 5. A force transducer 13 (for example of the kind supplied as type 8200 by Bruel and Kjaer) is mounted on a central spigot 14 attached to plate 11, and an impactor head 15 is mounted on the opposite face of transducer 13. Spring 12 has sufficient lateral stiffness to allow the system to operate in any orientation without coil 8 contacting magnet 5, and a test is carried out by causing source 10 to apply a current pulse to the coil, causing former 7 and all attached parts including head 15 to move towards structure 4. After impact, the same parts are returned to their original position by the force of spring 12, aided if required by a reverse pulse in coil 8. There must be sufficient damping in the system to prevent multiple impact. The output of transducer 13 is a voltage proportional to the instantaneous force of reaction experienced by impactor head 15.

Figure 5:
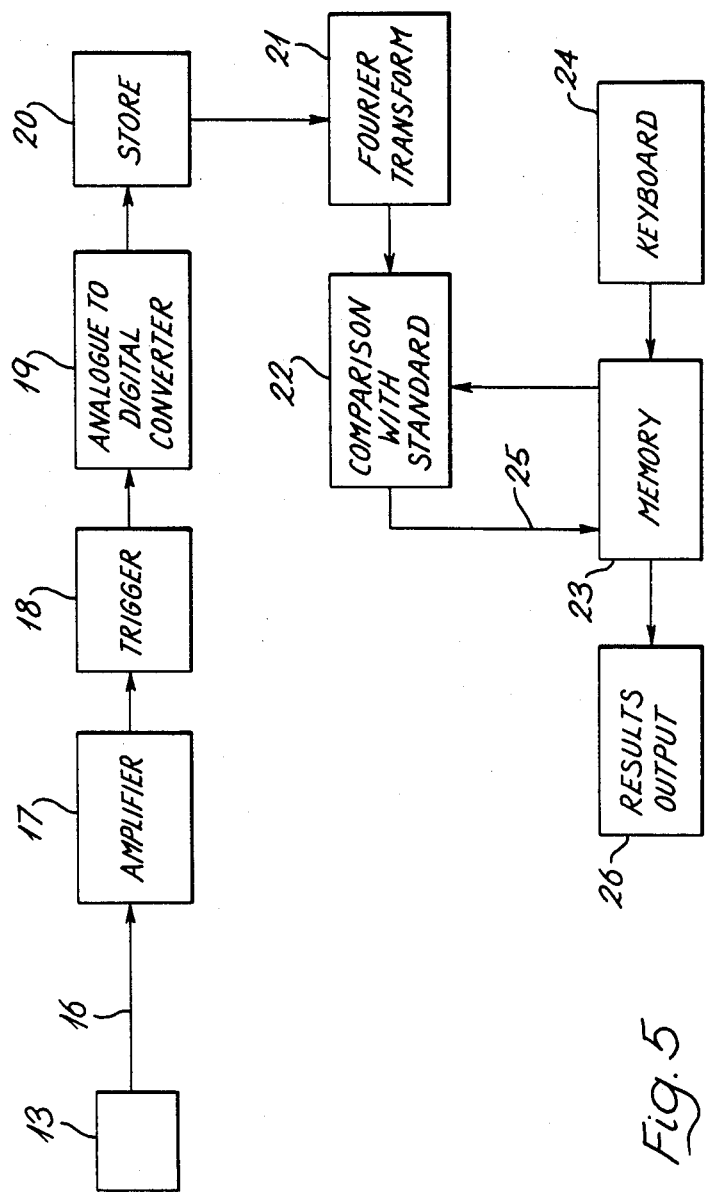

In block diagram form, FIG. 5 shows the necessary electronic circuit components. The output signals from force transducer 13 pass by way of leads 16 and an amplifier 17 and trigger unit 18 to an analogue-to-digital converter 19 and thence to an associated store 20. Trigger unit 18, of a kind standard in known spectrum analysers, operates when the signal from amplifier 17 exceeds a certain level, but also ensures that the value of the output of amplifier 17 for several points prior to the moment of trigger enters the store 20. The value of this facility is that the leading edge of the force pulse and therefore the information contained in this part of the force-time history is included in the frequency spectrum to be computed from that history.

When required, the output of store 20 is fed to a Fourier transform unit 21 where, because of the relatively short duration of the force pulse (as illustrated in FIGS. 1 and 2) a transform of only say thirty-two points may be needed to convert the output of store 20 into a digital frequency spectrum which may then be compared, in unit 22, with a reference frequency spectrum fed to unit 22 from a memory unit 23 into which it had itself been entered either by a test on a reference structure (which could itself have been a previous test structure) or by a keyboard 24 which may also be used to enter other instructions to set up the system. The result of the comparison is returned to memory 23 immediately by unit 26 and/or retained for subsequent use. Unit 26 may take various forms: for instance a red/green light, an alarm bell or a VDU display.

We claim:

1. A method of testing a structure by the use of an impactor attached to a force transducer comprising:
   causing the impactor to make impact with the structure;
   obtaining from the force transducer an output the magnitude of which is linearly related to the force to which the transducer is subjected by reason of the impact, the output encompassing a frequency range including the lowest frequencies which the force includes to any substantial degree;
   passing the output of the force transducer to a spectrum analyser to yield a test frequency spectrum of the output over the said frequency range in a form suitable for automatic comparison with a reference spectrum of similar form indicative of the same impactor striking a reference structure;
   so comparing the test and reference spectra automatically, and
   producing a signal indicative of a fit or lack of fit between the test and reference spectra.

2. A method of testing according to claim 1 in which the lower end of the frequency range is substantially zero frequency.

3. A method of testing according to claim 2 in which the upper end of the frequency range is about 30 kHz.

4. A method of testing according to claim 1 in which the output of the force transducer is passed to the spectrum analyser not only during the duration of the impact but also for a short period afterwards.

5. A method of testing according to claim 1 in which the spectra are presented in a form in which the force indicated on a logarithmic scale is plotted against frequency.

6. A method of testing according to claim 1 in which generation of the test spectrum is triggered by the magnitude of the output from the force transducer exceeding a preset value.

7. A method of testing according to claim 1 including a "pretrigger facility", whereby the test spectrum when generated includes information relating to a predetermined period occurring before the moment of triggering.

8. Apparatus for testing structures by impact comprising:

an impactor;

a force transducer associated with the impactor, and adapted when the impactor makes impact with a structure to produce an output the magnitude of which is linearly related to the force to which the force transducer is subjected by reason of the impact, the output emcompassing a frequency range including the lowest frequencies which the force includes to any substantial degree;

a spectrum analyser adapted to receive the output of the force transducer and produce a test frequency spectrum of that output;

means to produce a reference spectrum indicative of the frequency spectrum of the impactor striking a reference structure;

means to compare the test and reference spectra automatically, and means to produce a signal indicative of a fit or lack of fit between the test and reference spectra.

9. Apparatus according to claim 8, in which the spectrum analyser comprises the combination of an analogue-to-digital converter and a digital Fourier transformer adapted to receive the output of that converter.

* * * * *